United States Patent [19]

Becker et al.

[11] Patent Number: 4,500,340

[45] Date of Patent: Feb. 19, 1985

[54] UREA DERIVATIVES AND THEIR USE FOR CONTROLLING UNDESIRABLE PLANT GROWTH

[75] Inventors: Rainer Becker, Bad Durkheim; Hans Theobald, Limburgerhof; Ulrich Schirmer, Heidelberg; Wolfgang Spiegler; Walter Seufert, both of Ludwigshafen; Bruno Wuerzer, Otterstadt, all of Fed. Rep. of Germany

[73] Assignee: BASF Aktiengesellschaft, Fed. Rep. of Germany

[21] Appl. No.: 443,523

[22] Filed: Nov. 22, 1982

[30] Foreign Application Priority Data

Dec. 5, 1981 [DE] Fed. Rep. of Germany ....... 3148291

[51] Int. Cl.³ .................. C07D 277/62; C07D 333/14; C07D 277/20; A01N 47/30
[52] U.S. Cl. ............................................ 71/90; 71/88; 71/92; 548/128; 548/131; 548/136; 548/143; 548/180; 548/204; 548/236; 548/247; 548/269; 548/341; 548/378
[58] Field of Search ................. 564/20; 548/247, 236, 548/180, 204, 131, 143, 136, 128, 378, 341, 269; 71/88, 90, 92

[56] References Cited

U.S. PATENT DOCUMENTS

| 4,289,903 | 9/1981 | Spatz | 564/20 |
| 4,364,769 | 12/1982 | Pissiotas et al. | 71/90 |

FOREIGN PATENT DOCUMENTS

| 2950019 | 7/1980 | Fed. Rep. of Germany | 548/341 |
| 56-133282 | 10/1981 | Japan | 71/90 |
| 58-39656 | 3/1983 | Japan | 71/90 |
| 1284511 | 8/1972 | United Kingdom | 71/90 |
| 2012764 | 8/1979 | United Kingdom | 71/90 |

OTHER PUBLICATIONS

Chemical Abstracts, 96:68809h, Substituted Phenylurea Derivatives, vol. 96, 1982, p. 594.

*Primary Examiner*—Robert Gerstl
*Attorney, Agent, or Firm*—Keil & Weinkauf

[57] ABSTRACT

Urea derivatives of the formula

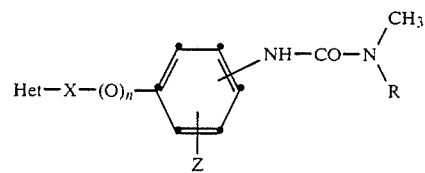

where R, X, Z, Het and n have the meanings given in the description, are used for controlling undesirable plant growth.

9 Claims, No Drawings

UREA DERIVATIVES AND THEIR USE FOR CONTROLLING UNDESIRABLE PLANT GROWTH

The present invention relates to urea derivatives, herbicides containing these compounds as active ingredients, and a method of controlling undesirable plant growth using these active ingredients.

Japanese Preliminary Published Application 81/133,282 discloses that N'-(thienyl-alkoxy-phenyl)-N-methyl-(methoxy)-N-methyl ureas have a herbicidal action.

We have found that urea derivatives of the formula

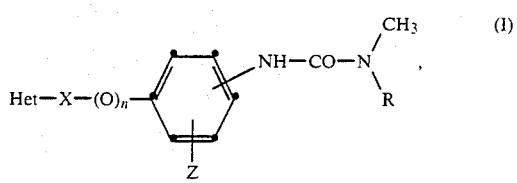

where
- R is hydrogen, or alkyl, alkenyl, alkynyl or alkoxy of not more than 4 carbon atoms,
- X is straight-chain or branched alkylene of not more than 4 carbon atoms,
- Z is hydrogen, halogen, methyl or trifluoromethyl and
- Het is a 5-membered heterocyclic radical of 1 to 4 hetero-atoms chosen from the group comprising oxygen, nitrogen and sulfur, with the exception of thienyl, and is unsubstituted or substituted by halogen, or by alkyl, haloalkyl, alkoxy, haloalkoxy, alkoxyalkyl or alkoxycarbonyl, each of not more than 5 carbon atoms, or by unsubstituted or substituted phenyl or by unsubstituted or substituted benzyl, or is a corresponding benzyl-fused 5-membered heterocyclic radical, which may be substituted in the same way, and
- n is 0 or 1, have a herbicidal action and are selective in crops.

In formula I, R is hydrogen, or alkyl, alkenyl, alkynyl or alkoxy of not more than 4 carbon atoms, eg. methyl, methoxy, ethoxy, allyl or 1-methyl-prop-2-ynyl, and is preferably methyl or methoxy, in particular methoxy.

X is straight-chain or branched alkylene of not more than 4 carbon atoms, eg. methylene, dimethylene, 1-methyl-dimethylene or trimethylene.

Z is hydrogen, methyl, trifluoromethyl or halogen, eg. chlorine, fluorine or bromine, especially chlorine.

Het is, for example, an isoxazole, oxazole, thiazole, oxadiazole, thiadiazole, pyrazole, imidazole, triazole, benzoxazole or benzothiazole ring, which may be substituted by halogen, eg. chlorine, fluorine or bromine, alkyl of not more than 5 carbon atoms, eg. methyl, ethyl, isopropyl or tert.-butyl, haloalkyl of not more than 5 carbon atoms, eg. trifluoromethyl, alkoxy of not more than 5 carbon atoms, eg. methoxy or ethoxy, haloalkoxy of not more than 5 carbon atoms, eg. difluoromethoxy or trifluoromethoxy, alkoxyalkyl of not more than 5 carbon atoms, eg. methoxymethyl, 2-methoxyethyl or ethoxymethyl, alkoxycarbonyl of not more than 5 carbon atoms, eg. methoxycarbonyl or ethoxycarbonyl, or phenyl or benzyl which is unsubstituted or substituted by halogen, eg. chlorine, alkyl, eg. methyl, alkoxy, eg. methoxy, or nitro.

Preferred compounds of the formula I are those in which Het is benzothiazolyl which is unsubstituted or substituted by halogen, or by alkyl, haloalkyl, alkoxy, haloalkoxy, alkoxyalkyl or alkoxycarbonyl, each of not more than 5 carbon atoms, or by unsubstituted or substituted phenyl, or by unsubstituted or substituted benzyl.

The compounds of the formula I in which n is 1 are obtained by reacting a compound of the formula

where Het and X have the above meanings and Hal is halogen, in particular chlorine, with a phenol of the formula

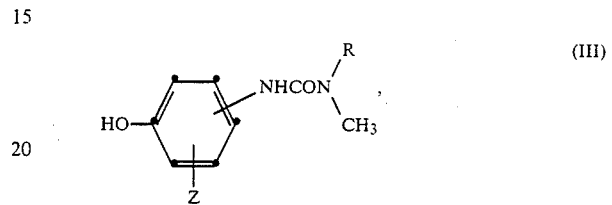

where R and Z have the above meanings, in an inert solvent at from 0° to 150° C., preferably from 50° to 100° C.

The reaction is preferably carried out in the presence of a base in an amount of from 1.0 to 1.5 moles, based on the compound of the formula II. Suitable bases are alkali metal carbonates, alkali metal bicarbonates and alkali metal hydroxides, eg. sodium carbonate, sodium bicarbonate, potassium carbonate, sodium hydroxide and potassium hydroxide.

Suitable solvents include polar organic solvents, eg. acetone, acetonitrile, dimethylformamide and dimethylsulfoxide, and water. If the reaction is carried out in an aqueous medium, it is advantageous to add a phase transfer catalyst, eg. tetrabutylammoniumiodide, in an amount of from about 0.01 to 0.1 mole, based on the compound of the formula II.

The reactants are reacted in an equimolar ratio, but an excess of one or other of the components does not present problems.

The compounds of the formula I in which n is 1 are also obtained by reacting a compound of the formula

where Het and X have the above meanings, with a halonitroaromatic of the formula

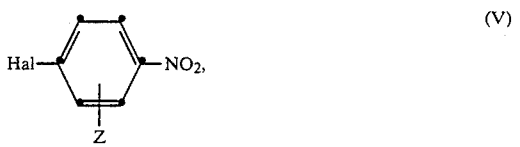

where
- Z has the above meanings and Hal is halogen, reducing the nitro compound and reacting the aniline derivative with
  - (a) an isocyanate of the formula RNCO, or
  - (b) a carbamyl chloride of the formula

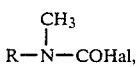

where
R in each formula has the above meanings and Hal is halogen. The aniline derivative can also be phosgenated and the product reacted with an amine of the formula HN(CH₃)R to give the urea derivative.

The compound of the formula IV is reacted with the compound of the formula V under the same conditions as those for the reaction of the compound of the formula II with the compound of the formula III.

The resulting nitro compound is reduced in a conventional manner, by catalytic hydrogenation with Raney nickel or Pd/C or by reaction with a reducing agent, eg. tin (II) chloride or iron powder in hydrochloric acid.

Conversion of the resulting aniline derivative into the urea is likewise effected in a conventional manner, by reaction with methylisocyanate in an inert solvent eg. acetone, acetonitrile, toluene or tetrahydrofuran, or by reaction with a carbamyl chloride in pyridine at from 0° to 50° C. or in an inert solvent, eg. acetone, tetrahydrofuran or acetonitrile, with the aid of a base, eg. triethylamine, pyridine, an alkali metal carbonate or an alkali metal bicarbonate.

Compounds of the formula I where n is 1 are also obtained by reacting a compound of the formula

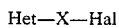 Het—X—Hal (VI), where
Het and X have the above meanings and Hal is halogen, with a nitrophenol derivative of the formula

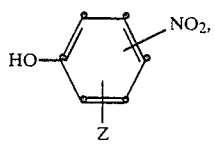 (VII)

where
Z has the above meanings, in an inert solvent at from 0° to 150° C., preferably from 50° to 100° C., reducing the nitro compound and reacting the aniline derivative with an isocyanate of the formula

RNCO or a carbamyl chloride of the formula

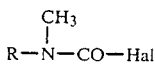

where
R in each formula has the above meanings and Hal is halogen, preferably chlorine. The aniline derivative can also be phosgenated and the product reacted with an amine of the formula HN(CH₃)R to give the urea derivative.

The compound of the formula VI is reacted with the compound of the formula VII under the same conditions as those for the reaction of the compound of the formula II with the compound of the formula III.

Compounds of the formula I where n is 0 are obtained by reacting an aldehyde of the formula

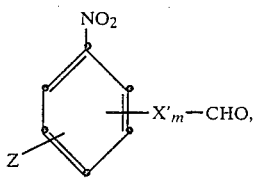

where
X' is straight-chain or branched alkylene of 1 or 2 carbon atoms, m is 0 or 1 and Z has the above meanings, with an active methylene compound of the formula

 Het—CH₃ (IX), where
Het has the above meanings, subsequently hydrogenating the product and reacting the hydrogenation product with a carbamyl halide of the formula

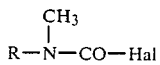

or with an isocyanate of the formula

RNCO where R in each formula has the above meanings and Hal is halogen, preferably chlorine.

The aldehyde of the formula VIII is reacted with the methylene compound of the formula IX in an inert solvent, eg. acetic acid with the addition of acetic anhydride, at from 50° to 150° C. The reactants are employed in an equimolar ratio, but an excess of one or other of the components presents no problems.

The resulting nitro compound is reduced in a conventional manner, by catalytic hydrogenation with addition of, for example, Raney nickel or Pd/C, and the C-C double bond is also hydrogenated in the course of this reaction.

Conversion of the resulting aniline derivative into the urea is likewise effected in a conventional manner, by reaction with methylisocyanate in an inert solvent, eg. toluene, acetone or acetonitrile, or by reaction with a carbamyl chloride in pyridine at from 0° to 5° C. or in an inert solvent, eg. acetone, tetrahydrofuran or acetonitrile, with the aid of an organic base, eg. triethylamine or pyridine, or an inorganic base, eg. an alkali metal carbonate or alkali metal bicarbonate.

Compounds of the formula I where n is 0 and Het is an unsubstituted or substituted pyrazole or isoxazole ring can be prepared from an aldehyde of the formula

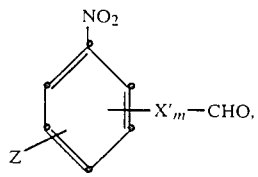

where X' is straight-chain or branched alkylene of 1 or 2 carbon atoms, m is 0 or 1 and Z has the above meanings, and an activated methylene compound of the formula

  (X)

where
R$^1$ and R$^2$ are each alkyl of not more than 5 carbon atoms, with subsequent hydrogenation and reaction of the hydrogenation product with a hydrazine derivative of the formula NH$_2$NHR$^3$, where R$^3$ is hydrogen, alkyl or phenyl, or with hydroxylamine.

The compound of the formula VIII is reacted with the compound of the formula X in an inert solvent, eg. toluene, with addition of a catalytic amount of, for example, glacial acetic acid/piperidine at from 50° to 150° C., the water being removed from the system. The unsaturated compound thereby obtained as the intermediate

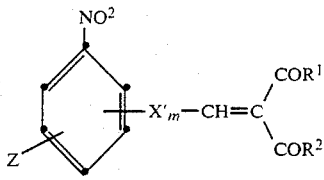

is hydrogenated in a conventional manner with Raney nickel or Pd/C and the hydrogenation product is then cyclized with hydrazine or a substituted hydrazine of the formula NH$_2$NHR$^3$, where R$^3$ is hydrogen, alkyl or phenyl, or with hydroxylamine. The resulting aniline can be converted into the urea of the formula I by the methods described above.

The Examples which follow illustrate the procedure for the processes according to the invention. Parts by weight bear the same relation to parts by volume as that of the kilogram to the liter.

EXAMPLE 1

138 parts by weight of potassium carbonate were added to 113 parts by weight of 3-methyl-5-hydroxymethylisoxazole and 141 parts by weight of p-fluoronitrobenzene in 200 parts by volume of dimethylformamide, and the mixture was stirred at 135° C. for 20 hours. After it had cooled, the mixture was stirred into ice-water and the 4-(3-methyl-isoxazol-5-yl-methoxy)-nitrobenzene was filtered off with suction.
Yield: 201 g; melting point: 127°–128° C.
C$_{11}$H$_{10}$N$_2$O$_4$/molecular weight=234
Calculated: C 56.41%, H 4.30%, N 11.96%,
Found: C 56.7%, H 4.3%, N 11.9%.

220 parts by weight of 4-(3-methyl-isoxazol-5-yl-methoxy)-nitrobenzene were suspended in 365 parts by weight of ethanol and 446 parts by weight of concentrated hydrochloric acid, and 767 g of SnCl$_2$.2H$_2$O were added a little at a time, while the temperature was kept at from 50° to 60° C. The mixture was then stirred for a further 2 hours at 60° C., and the resulting solution was stirred into 2,480 parts by weight of ice and 1,622 parts by weight of 50% strength sodium hydroxide solution. The 4-(3-methyl-isoxazol-5-yl-methoxy)-aniline was then filtered off.
Yield: 139 g; melting point: 67°–69° C.
C$_{11}$H$_{12}$N$_2$O$_2$/molecular weight=204
Calculated: C 64.69% H 5.92% N 13.72%,
Found: C 64.1% H 5.8% N 13.6%.

20.4 parts by weight of 4-(3-methyl-isoxazol-5-yl-methoxy)-aniline were dissolved in 150 parts by volume of pyridine, and 10.8 parts by weight of dimethylcarbamyl chloride were added dropwise at 20° C. After 20 hours, the mixture was stirred into ice-water/hydrochloric acid and the N-[4-(3-methyl-isoxazol-5-yl-methoxy)-phenyl]-N',N'-dimethyl urea was filtered off with suction.
Yield: 14.1 g;
melting point: 121°–122° C.
C$_{14}$H$_{17}$N$_3$O$_3$/molecular weight=275
Calculated: C 61.08%, H 6.22%, N 15.26%,
Found: C 61.5%, H 5.9%, N 14.6%.

EXAMPLE 2

13.3 parts by weight of 2-methyl-5-chloromethyl-1,3,4-oxadiazole in 200 parts by volume of acetone were refluxed with 18 parts by weight of N-(3-hydroxyphenyl)-N',N'-dimethyl urea and 13.8 g of potassium carbonate for 7 hours.

After the mixture had cooled, it was stirred into ice-water and filtered with suction. 15.6 g of N-[3-(2-methyl-1,3,4-oxadiazol-5-yl-methoxy)-phenyl]-N',N'-dimethyl urea of melting point 102°–105° C. were obtained.
C$_{13}$H$_{16}$N$_4$O$_3$/molecular weight=276
Calculated: C 56.51%, H 5.84%, N 20.28%,
Found: C 56.1%, H 5.8%, N 19.5%.

EXAMPLE 3

149 parts by weight of 2-methylbenzothiazole and 151 parts by weight of 4-nitrobenzaldehyde were dissolved in a mixture of 400 parts by volume of glacial acetic acid and 400 parts by volume of acetic anhydride, and the solution was stirred at 130° C. for 5 hours. It was then cooled to 70° C., and 800 ml of ethanol were carefully added. The resulting mixture was cooled and filtered with suction.
Yield: 168 g of β-(benzothiazol-2-yl)-4-nitrostyrene of melting point 235°–237° C.
C$_{15}$H$_{10}$N$_2$SO$_2$/molecular weight=282
Calculated: C 63.82%, H 3.57%, N 9.92%, S 11.36%,
Found: C 64.1%, H 3.6%, N 9.9%, S 11.2%.

150 parts by weight of β-(benzothiazol-2-yl)-4-nitrostyrene were dissolved in 1,500 parts by volume of tetrahydrofuran, and 15 parts by weight of Pd/C (10%) were added. After the mixture had been flushed with nitrogen, hydrogen was passed in. After some hours, the uptake of hydrogen (44 1) had ended, and the mixture was flushed with nitrogen again, the catalyst was filtered off and the filtrate was concentrated. 135.6 g of 4-(β-benzothiazol-2-yl-ethyl)-aniline of melting point 79°–81° C. were obtained.

25.4 parts by weight of 4-(β-benzothiazol-2-yl-ethyl)-aniline were dissolved in 150 parts by volume of tetrahydrofuran, and 13.8 parts by weight of potassium carbonate were added. 13.6 parts by weight of N-methyl-N-methoxycarbamyl chloride were then added dropwise. After the mixture had been stirred for several hours, it was poured into ice-water and extracted with methylene chloride, and the extract was concentrated.

The resulting solid was recrystallized from cyclohexane.

Yield: 23.3 g of N-[4-(β-benzothiazol-2-yl)-ethyl-phenyl]-N'-methyl-N'-methoxy urea of melting point 85°–87° C.

$C_{18}H_{19}N_3O_2S$/molecular weight = 341
Calculated: C 63.32%, H 5.61%, N 12.31%, S 9.39%,
Found: C 63.3%, H 5.5%, N 12.1%, S 9.8%.

The following compounds of the formula I can be prepared by the methods described above:

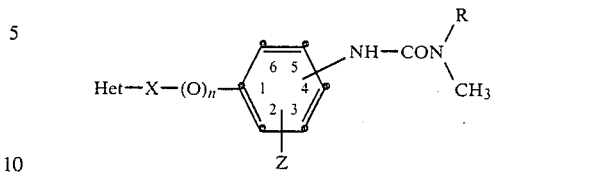

| Compound no. | Het | X | n | Z | Position of urea group | R | M.p. [°C.] |
|---|---|---|---|---|---|---|---|
| 1 | benzothiazolyl-2 | —CH₂—CH₂— | 0 | H | 3 | CH₃ | 137–139 |
| 2 | 5-phenyl-1,2,4-oxadiazolyl-3 | —CH₂— | 1 | H | 3 | OCH₃ | |
| 3 | 5-methyl-1,3,4-thiadiazolyl-2 | —CH₂— | 1 | H | 4 | OCH₃ | 139–145 |
| 4 | 3-tert.-butylisoxazolyl-5 | —CH₂—CH₂— | 1 | H | 4 | OCH₃ | |
| 5 | 3-methylisoxyzolyl-5 | —CH(CH₃)— | 1 | H | 4 | CH₃ | viscous oil |
| 6 | 5-phenyl-1,2,4-oxadiazolyl-3 | —CH₂— | 1 | H | 4 | OCH₃ | |
| 7 | 2-phenylthiazolyl-4 | —CH₂— | 1 | H | 4 | OCH₃ | 94–96 |
| 8 | 1-phenyl-3,5-dimethyl-pyrazolyl-4 | —CH₂— | 0 | H | 4 | OCH₃ | |
| 9 | benzothiazolyl-2 | —CH₂—CH₂— | 0 | H | 3 | OCH₃ | 95–98 |
| 10 | 1,3,5-trimethyl-pyrazolyl-4 | —CH₂— | 0 | H | 4 | OCH₃ | |
| 11 | 5-methyl-1,3,4-oxadiazolyl-2 | —CH₂— | 1 | H | 3 | CH₃ | 102–105 |
| 12 | 3-methyl-1,2,4-thiadiazolyl-5 | —CH₂— | 1 | H | 4 | OCH₃ | |
| 13 | 3-methyl-isoxazolyl-5 | —CH(CH₃)— | 1 | H | 4 | OCH₃ | viscous oil |
| 14 | 1,3,5-trimethylpyrazolyl-4 | —CH₂CH₂— | 0 | H | 4 | OCH₃ | |
| 15 | 3-tert.-butyl-isoxazolyl-5 | —CH₂— | 1 | H | 4 | CH₃ | 125–128 |
| 16 | 5-phenyl-1,2,4-oxadiazolyl-3 | —CH₂— | 1 | H | 4 | CH₃ | |
| 17 | 3-phenyl-isoxazolyl-5 | —CH₂— | 1 | H | 4 | OCH₃ | 123–125 |
| 18 | 3-methylisoxazolyl-5 | —CH₂CH₂— | 1 | H | 4 | OCH₃ | |
| 19 | 3-methylisoxazolyl-5 | —CH₂— | 1 | 2-Cl | 4 | CH₃ | 130–131 |
| 20 | 3-tert.-butyl-isoxazolyl-5 | —CH₂CH₂CH₂— | 0 | H | 4 | OCH₃ | |
| 21 | 3-methylisoxazolyl-5 | —CH₂— | 1 | H | 3 | CH₃ | 147–148 |
| 22 | 5-tert.-butyl-1,2,4-oxadiazolyl-3 | —CH₂— | 1 | H | 4 | OCH₃ | |
| 23 | 3-ethylisoxazolyl-5 | —CH₂— | 1 | H | 4 | CH₃ | 119–120 |
| 24 | 3-tert.-butyl-isoxazolyl-5 | —CH₂CH₂— | 1 | H | 4 | CH₃ | |
| 25 | 5-methyl-1,3,4-thiadiazolyl-2 | —CH₂— | 1 | H | 4 | CH₃ | 168–171 |
| 26 | benzothiazolyl-2 | —CH₂CH₂— | 0 | H | 4 | CH₃ | 170–172 |
| 28 | 5-methyl-1,3,4-thiadiazolyl-2 | —CH₂— | 1 | H | 3 | CH₃ | 155–157 |
| 29 | 1-phenyl-3,5-dimethylpyrazolyl-4 | —CH₂— | 0 | H | 3 | OCH₃ | oil |
| 30 | isoxazolyl-5 | —CH₂— | 1 | H | 4 | OCH₃ | 109–111 |
| 31 | 5-methyl-1,2,4-oxadiazolyl-3 | —CH₂— | 1 | H | 4 | CH₃ | |
| 32 | 3-methylisoxazolyl-5 | —CH₂— | 1 | H | 4 | H | 176–180 |
| 33 | 3-methylisoxazolyl-5 | —CH₂CH₂— | 1 | H | 4 | CH₃ | |
| 34 | 3-ethoxycarbonyl-isoxazolyl-5 | —CH₂— | 1 | H | 4 | OCH₃ | 72–75 |
| 35 | benzothiazolyl-2 | —CH₂— | 1 | H | 4 | OCH₃ | |
| 36 | 3-methylisoxazolyl-5 | —CH₂— | 1 | H | 3 | OCH₃ | 91–92 |
| 37 | 5-methyl-1,2,4-oxadiazolyl-3 | —CH₂— | 1 | H | 4 | OCH₃ | |
| 38 | 5-methyl-1,3,4-oxadiazolyl-2 | —CH₂— | 1 | H | 4 | OCH₃ | 90–93 |
| 40 | 3-(4-chlorophenyl)-isoxazolyl-5 | —CH₂— | 1 | H | 4 | CH₃ | 201–203 |
| 41 | 4,5-dichloroimidazolyl | —CH₂CH₂— | 1 | H | 4 | OCH₃ | 151–153 |
| 42 | 3-methoxymethylisoxazolyl-5 | —CH₂— | 1 | H | 4 | H | 100–101 |
| 43 | 3-methylisoxazolyl-5 | —CH₂— | 1 | 2-CF₃ | 4 | CH₃ | |
| 44 | 3-phenylisoxazolyl-5 | —CH₂— | 1 | H | 4 | CH₃ | 165–167 |

-continued

| Compound no. | Het | X | n | Z | Position of urea group | R | M.p. [°C.] |
|---|---|---|---|---|---|---|---|
| 45 | 1,3,5-trimethyl-pyrazolyl-4 | —CH$_2$CH$_2$CH$_2$— | 0 | H | 4 | OCH$_3$ | |
| 46 | 3-ethylisoxyzolyl-5 | —CH$_2$— | 1 | H | 4 | OCH$_3$ | 72–73 |
| 47 | 1-phenyl-3,5-dimethylpyrazolyl-4 | —CH$_2$— | 0 | H | 4 | CH$_3$ | |
| 48 | 2-methylthiazolyl-4 | —CH$_2$— | 1 | H | 4 | OCH$_3$ | 65–67 |
| 49 | benzothiazolyl-2 | —CH$_2$CH$_2$CH$_2$— | 0 | H | 4 | OCH$_3$ | |
| 50 | 3-methylisoxazolyl-5 | —CH$_2$— | 1 | H | 4 | OCH$_3$ | 109–112 |
| 51 | 1,3,5-trimethyl-pyrazolyl-4 | —CH$_2$CH$_2$CH$_2$— | 0 | H | 4 | CH$_3$ | |
| 52 | 3-methylisoxazolyl-5 | —CH$_2$— | 1 | 2-Cl | 4 | OCH$_3$ | 141–142 |
| 53 | 3,5-dimethyl-isoxazolyl-4 | —CH$_2$CH$_2$CH$_2$— | 0 | H | 4 | OCH$_3$ | |
| 54 | 1,3,5-trimethyl-pyrazolyl-4 | —CH$_2$— | 0 | H | 3 | OCH$_3$ | 108–110 |
| 55 | 3-methylisoxazolyl-5 | —CH$_2$— | 1 | 2-CF$_3$ | 4 | OCH$_3$ | 105–107 |
| 56 | 3-methylisoxazolyl-5 | —CH$_2$— | 1 | H | 4 | CH$_3$ | 121–122 |
| 57 | 3,5-dimethylisoxazolyl-4 | —CH$_2$— | 0 | H | 4 | CH$_3$ | |
| 58 | isoxazolyl-5 | —CH$_2$— | 1 | H | 4 | H | 135–136 |
| 59 | 3,5-dimethylisoxazolyl-4 | —CH$_2$CH$_2$— | 0 | H | 4 | OCH$_3$ | |
| 60 | 3-ethyloxadiazolyl-5 | —CH$_2$— | 1 | H | 4 | H | 144–146 |
| 61 | 4,5-dichloroimidazolyl-1 | —CH$_2$CH$_2$— | 1 | H | 4 | CH$_3$ | 170–172 |
| 62 | 3-(4-chlorophenyl)-isoxazolyl-5 | —CH$_2$— | 1 | H | 4 | OCH$_3$ | 152–154 |
| 63 | imidazolyl | —CH$_2$CH$_2$— | 1 | H | 4 | OCH$_3$ | |
| 64 | 3-tert.-butylisoxazolyl-5 | —CH$_2$— | 1 | H | 4 | OCH$_3$ | 84–85 |
| 65 | 3-tert.-butyl-isoxazolyl-5 | —CH$_2$CH$_2$CH$_2$— | 0 | H | 3 | OCH$_3$ | |
| 66 | 3,5-dimethylisoxazolyl-4 | —CH$_2$— | 1 | H | 3 | OCH$_3$ | 112–114 |
| 67 | 1,2,4-triazolyl | —CH$_2$CH(CH$_3$)— | 1 | H | 4 | OCH$_3$ | |
| 68 | 3-isopropylisoxazolyl-5 | —CH$_2$— | 1 | H | 4 | H | 111–113 |
| 69 | benzothiazolyl-2 | —CH$_2$CH$_2$— | 1 | H | 4 | OCH$_3$ | |
| 70 | isoxazolyl-5 | —CH$_2$— | 1 | H | 4 | CH$_3$ | 112–113 |
| 71 | 3,5-dimethylisoxazolyl-4 | —CH$_2$— | 0 | H | 4 | OCH$_3$ | |
| 72 | 2-methylthiazolyl-4 | —CH$_2$— | 1 | H | 3 | OCH$_3$ | 115–117 |
| 73 | 3-tert.-butyl-isoxazolyl-5 | —CH$_2$CH$_2$CH$_2$— | 0 | H | 4 | CH$_3$ | |
| 74 | 3-methylisoxazolyl-5 | —CH$_2$— | 1 | 2-CH$_3$ | 4 | OCH$_3$ | |
| 75 | benzothiazolyl-2 | —CH$_2$CH$_2$— | 0 | H | 4 | OCH$_3$ | 85–87 |
| 76 | 3,5-dimethylisoxazolyl-4 | —CH$_2$CH$_2$CH$_2$— | 0 | H | 3 | OCH$_3$ | |
| 77 | 3,5-dimethylisoxazolyl-4 | —CH$_2$CH$_2$CH$_2$— | 0 | H | 3 | CH$_3$ | |
| 78 | 1,3,5-trimethyl-pyrazolyl-4 | —CH$_2$CH$_2$CH$_2$— | 0 | H | 3 | OCH$_3$ | |
| 79 | 1,3,5-trimethyl-pyrazolyl-4 | —CH$_2$CH$_2$CH$_2$— | 0 | H | 3 | CH$_3$ | |
| 80 | 2-(4-chlorobenzyl)-thiazolyl-4 | —CH$_2$— | 1 | H | 3 | OCH$_3$ | 97–99 |
| 81 | 2-(4-chlorobenzyl)-thiazolyl-4 | —CH$_2$— | 1 | H | 3 | CH$_3$ | |
| 82 | 2-(4-chlorobenzyl)-thiazolyl-4 | —CH$_2$— | 1 | H | 4 | OCH$_3$ | 110–112 |
| 83 | 2-(4-chlorobenzyl)-thiazolyl-4 | —CH$_2$— | 1 | H | 4 | CH$_3$ | |
| 84 | 2-(4-chlorophenyl)-thiazolyl-4 | —CH$_2$— | 1 | H | 3 | OCH$_3$ | 116–117 |
| 85 | 2-(4-chlorophenyl)-thiazolyl-4 | —CH$_2$— | 1 | H | 3 | CH$_3$ | |
| 86 | 2-(4-chlorophenyl)-thiazolyl-4 | —CH$_2$— | 1 | H | 4 | OCH$_3$ | 147–149 |
| 87 | 2-(4-chlorophenyl)-thiazolyl-4 | —CH$_2$— | 1 | H | 4 | CH$_3$ | |
| 88 | 2-(4-methoxyphenyl)-thiazolyl-4 | —CH$_2$— | 1 | H | 3 | OCH$_3$ | 111–114 |
| 89 | 2-(4-methoxyphenyl)-thiazolyl-4 | —CH$_2$— | 1 | H | 3 | CH$_3$ | |
| 90 | 2-(4-methoxyphenyl)-thiazolyl-4 | —CH$_2$— | 1 | H | 4 | OCH$_3$ | 130–132 |
| 91 | 2-(4-methoxyphenyl)-thiazolyl-4 | —CH$_2$— | 1 | H | 4 | CH$_3$ | |
| 92 | 2-(3-methylphenyl)- | —CH$_2$— | 1 | H | 3 | OCH$_3$ | 107–108 |

-continued

| Compound no. | Het | X | n | Z | Position of urea group | R | M.p. [°C.] |
|---|---|---|---|---|---|---|---|
| 93 | 2-(3-methylphenyl)-thiazolyl-4 | —CH₂— | 1 | H | 3 | CH₃ | |
| 94 | 2-(3-methylphenyl)-thiazolyl-4 | —CH₂— | 1 | H | 4 | OCH₃ | 123–125 |
| 95 | 2-(3-methylphenyl)-thiazolyl-4 | —CH₂— | 1 | H | 4 | CH₃ | |
| 96 | 2-(2-chlorophenyl)-thiazolyl-4 | —CH₂— | 1 | H | 3 | OCH₃ | |
| 97 | 2-(2-chlorophenyl)-thiazolyl-4 | —CH₂— | 1 | H | 3 | CH₃ | |
| 98 | 2-(2-chlorophenyl)-thiazolyl-4 | —CH₂— | 1 | H | 4 | OCH₃ | 130–132 |
| 99 | 2-(2-chlorophenyl)-thiazolyl-4 | —CH₂— | 1 | H | 4 | CH₃ | |
| 100 | 3-(4-nitrophenyl)-1,2,4-oxadiazolyl-5 | —CH₂— | 1 | H | 4 | OCH₃ | 188–190 |
| 101 | 3-(4-nitrophenyl)-1,2,4-oxadiazolyl-5 | —CH₂— | 1 | H | 3 | CH₃ | |
| 102 | 3-(4-chlorophenyl)-1,2,4-oxadiazolyl-5 | —CH₂— | 1 | H | 3 | OCH₃ | |
| 103 | 3-(4-chlorophenyl)-1,2,4-oxadiazolyl-5 | —CH₂— | 1 | H | 3 | CH₃ | |
| 104 | 3-(4-chlorophenyl)-1,2,4-oxadiazolyl-5 | —CH₂— | 1 | H | 4 | OCH₃ | 140–142 |
| 105 | 3-(4-chlorophenyl)-1,2,4-oxadiazolyl-5 | —CH₂— | 1 | H | 4 | CH₃ | |
| 106 | 3-methylisoxazolyl-5 | —CH₂— | 1 | 2-Cl | 4 | OC₂H₅ | 77–79 |
| 107 | 3-methylisoxazolyl-5 | —CH₂— | 1 | 2-Cl | 4 | C₂H₅ | |
| 108 | 3-methylisoxazolyl-5 | —CH₂— | 1 | 2-Cl | 4 | CH₂CH=CH₂ | |
| 109 | 3-methylisoxazolyl-5 | —CH₂— | 1 | 2-Cl | 4 | CH(CH₃)C CH | |
| 110 | 3-methylisoxazolyl-5 | —CH₂— | 1 | 2-CF₃ | 4 | OC₂H₅ | |
| 111 | 2-(4-chlorophenyl)-thiazol-4-yl | —CH₂— | 1 | 2-Cl | 4 | OCH₃ | 160–161 |
| 112 | 2-(4-chlorobenzyl)-thiazol-4-yl | —CH₂— | 1 | 2-Cl | 4 | OCH₃ | 114–115 |
| 113 | imidazolyl | —CH₂—CH(CH₃)—CH₂— | 0 | H | 4 | OCH₃ | oil |
| 114 | 4-methylthiazol-5-yl | —CH₂CH₂— | 1 | H | 4 | OCH₃ | 120–122 |
| 115 | 4-methylthiazol-5-yl | —CH₂CH₂— | 1 | H | 4 | CH₃ | 111–112 |
| 116 | 4-methylthiazol-5-yl | —CH₂CH₂— | 1 | 2-Cl | 4 | OCH₃ | 128–130 |
| 117 | 4-methylthiazol-5-yl | —CH₂CH₂— | 1 | 2-Cl | 4 | CH₃ | 110–112 |
| 118 | 4-methylthiazol-5-yl | —CH₂CH₂— | 1 | 2-CF₃ | 4 | OCH₃ | 87–89 |
| 119 | 4-methylthiazol-5-yl | —CH₂CH₂— | 1 | 2-CF₃ | 4 | CH₃ | 90–93 |
| 120 | 1,2,4-triazolyl | —CH₂CH₂— | 1 | H | 4 | OCH₃ | 117–118 |
| 121 | 1,2,4-triazolyl | —CH₂CH₂— | 1 | H | 4 | CH₃ | 136–138 |
| 122 | 3-methylisoxazolyl-5-yl | —CH₂— | 1 | 2-Br | 4 | OCH₃ | 130–133 |
| 123 | 3-methylisoxazolyl-5-yl | —CH₂— | 1 | 3-Br | 4 | OCH₃ | 91–93 |
| 124 | 3-methylisoxazolyl-5-yl | —CH₂— | 1 | H | 3 | OC₂H₅ | 94–96 |
| 125 | 3-phenyl-1,2,4-oxadiazol-5-yl | —CH₂— | 1 | H | 4 | OCH₃ | 107–109 |
| 126 | 2-methylthiazol-4-yl | —CH₂— | 1 | 2-Cl | 4 | OCH₃ | 99–101 |
| 127 | 2-methylthiazol-4-yl | —CH₂— | 1 | 2-Br | 4 | OCH₃ | 102–104 |
| 128 | 2-methylthiazol-4-yl | —CH₂— | 1 | 2-CF₃ | 4 | OCH₃ | 119–122 |
| 129 | 5-trifluoromethyl-benzothiazol-2-yl | —CH₂CH₂— | 0 | H | 4 | CH₃ | |
| 130 | 5-trifluoromethyl-benzothiazol-2-yl | —CH₂CH₂— | 0 | H | 4 | OCH₃ | |
| 131 | 5-trifluoromethyl-benzothiazol-2-yl | —CH₂CH₂— | 0 | H | 3 | CH₃ | |
| 132 | 5-trifluoromethyl-benzothiazol-2-yl | —CH₂CH₂— | 0 | H | 3 | OCH₃ | |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredient as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated napththalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 5 is mixed with 10 parts by weight of N-methyl-alpha-pyrrolidone. A mixture is obtained which is suitable for application in the form of very fine drops.

II. 20 parts by weight of compound no. 13 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 19 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 50 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 64 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 36 is intimately mixed with 97 parts by weight of particulate kaolin. A dust is obtained containing 3% by weight of the active ingredient.

VII. 30 parts by weight of compound no. 46 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 23 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

The active ingredients, or formulations containing them, may be applied pre- or postemergence. Preferably, the novel active ingredients are applied during or after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year and the growth stage of the plants, and varies from 0.025 to 10 kg/ha and more, but is preferably from 0.1 to 4 kg/ha. The higher application rates are particularly suitable for total elimination of vegetation.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rates varied from compound to compound, and were approx. 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. In the case of soybeans used for the postemergence treatment, peat was added to the substrate to ensure better growth. For this treatment, either plants which had been sown directly in the pots and grown there were selected, or plants which had been grown separately as seedlings and transplanted to the experiment vessels a few days before treatment. The application rates for postemergence treatment varied from ingredient to ingredient, and were either 0.125, 0.25, 0.5 or or 1.0 kg of active ingredient per hectare. No covers were placed on the vessels in this treatment.

The pots were set up in the greenhouse—species from warmer areas at from 20° to 30° C., and species from moderate climates at 15° to 25° C. The experiments were run for from 3 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants were *Alopecurus myosuroides, Amaranthus retroflexus, Arachys hypogaea, Avena fatua, Chenopodium album, Desmodium tortuosum, Echinochloa crusgalli, Euphorbia geniculata, Galium aparine, Glycine max., Gossypium hirsutum, Ipomoea spp., Lamium spp., Lolium multiflorum, Mercurialis annua, Nicandra physaloides, Sesbania exaltata, Sinapis alba, Solanum nigrum, Triticum aestivum, Setaria italica, Sida spinosa,* and *Viola tricolor.*

On preemergence application, for example compounds nos. 50, 56, 36, 52, 46, 21, 19, 5, 23, 64, 13 and 48, at a rate of 3.0 kg/ha, had a considerable herbicidal action.

On postemergence application, for example compounds nos. 1, 9, 26 and 64 at a rate of 0.5 kg, and no. 46 at a rate of 1.0 kg/ha, selectively combated a large number of unwanted plants. Compounds nos. 15, 48 and 50 at 0.5 kg/ha, compounds nos. 36 and 21 at 0.25 kg/ha and compounds nos. 19 and 23 at 0.125 kg/ha also had a selective herbicidal action on postemergence application. Compound no. 52, applied postemergence at low rates, had a very good action on unwanted broadleaved plants. At a rate of 3.0 kg/ha, compounds nos. 7, 29, 38, 72, 75, 94, 106, 124 and 125 had a very good herbicidal action.

In view of the tolerance of the compounds of the formula I, or mixtures containing them, and the many application methods possible, they can be used in a further, large number of crops for removing unwanted plant growth.

The following crops may be mentioned by way of example:

| Botanical name | Common name |
|---|---|
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |

-continued

| Botanical name | Common name |
|---|---|
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A urea derivative of the formula

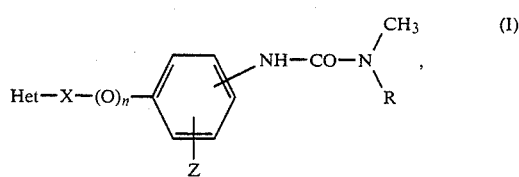

where
R is hydrogen, or alkyl, alkenyl, alkynyl or alkoxy of not more than 4 carbon atoms,
X is straight-chain or branched alkylene of not more than 4 carbon atoms,
Z is hydrogen, halogen, methyl or trifluoromethyl and Het is an isoxazole, oxazole, thiazole, oxadiazole, thiadiazole, pyrazole or triazole ring, unsubstituted or substituted by halogen, or by alkyl, haloalkyl, alkoxy, haloalkoxy, alkoxyalkyl or alkoxycarbonyl, each of not more than 5 carbon atoms, or by phenyl, by phenyl substituted by halogen, alkyl, alkoxy or nitro, by benzyl or by benzyl substituted by halogen, alkyl, alkoxy or nitro, or is a corresponding benzyl-fused benzothiazoyl radical, which may substituted in the same way,
and
n is 0 or 1.

2. A urea derivative of the formula I as described in claim 1, where Het is benzthiazolyl which is unsubstituted or substituted by halogen, alkyl, haloalkyl, alkoxy, haloalkoxy, alkoxyalkyl or alkoxycarbonyl, each of not more than 5 carbon atoms, or by phenyl, by phenyl substituted by halogen, alkyl, alkoxy or nitro, by benzyl or by benzyl substituted by halogen, alkyl, alkoxy or nitro.

3. N-[3-(2-(Benzthiazol-2-yl)-ethoxy)-phenyl]-N'-methoxy-N'-methylurea.

4. A herbicide containing inert additives and from 0.1 to 95% by weight of a urea derivative of the formula I as described in claim 1.

5. A herbicide as set forth in claim 4, wherein the Het group of the urea derivative is benzthiazolyl which is unsubstituted or substituted by halogen, alkyl, haloalkyl, alkoxy, haloalkoxy, alkoxyalkyl or alkoxycarbonyl, each of not more than 5 carbon atoms, or by phenyl, by phenyl substituted by halogen, alkyl, alkoxy or nitro, by benzyl or by benzyl substituted by halogen, alkyl, alkoxy or nitro.

6. A process for combating unwanted plant growth, wherein the unwanted plants or the area to be kept free from unwanted plant growth are treated with a herbicidally effective amount of a urea derivative of the formula I as described in claim 1.

7. A urea derivative as described in claim 1, wherein the Het group is substituted by phenyl or benzyl which are unsubstituted or substituted by chlorine, methyl, methoxy or nitro.

8. A urea dervative as described in claim 1, wherein R is methyl or methoxy.

9. A urea derivative of the formula I, as defined in claim 1, wherein Het is an isoxazole, oxadiazole, thiazole, pyrazole or benzothiazole ring which is unsubstituted or substituted by alkyl, phenyl or alkyl-substituted phenyl.

* * * * *